United States Patent [19]

Abe

[11] 4,367,018
[45] Jan. 4, 1983

[54] EYEBALL MICROSCOPE

[75] Inventor: Kuniomi Abe, Kobe, Japan

[73] Assignee: Konan Camera Research Institute, Hyogo, Japan

[21] Appl. No.: 139,142

[22] Filed: Apr. 10, 1980

[30] Foreign Application Priority Data

| May 8, 1979 | [JP] | Japan | 54-56560 |
| May 8, 1979 | [JP] | Japan | 54-61440[U] |
| Nov. 5, 1979 | [JP] | Japan | 54-143625 |
| Nov. 5, 1979 | [JP] | Japan | 54-153887[U] |
| Nov. 5, 1979 | [JP] | Japan | 54-153888[U] |
| Dec. 20, 1979 | [JP] | Japan | 54-177512[U] |

[51] Int. Cl.³ ................... A61B 3/14; A61B 3/10
[52] U.S. Cl. .................................... 351/213; 351/205
[58] Field of Search .................. 351/6; 350/418, 447

[56] References Cited

U.S. PATENT DOCUMENTS

| 1,954,755 | 4/1934 | Heine | 350/447 X |
| 3,409,349 | 11/1968 | Boyle et al. | 351/6 |
| 4,061,423 | 12/1977 | Pomerantzeff | 351/16 |
| 4,067,646 | 1/1978 | Nohda | 351/16 X |

OTHER PUBLICATIONS

Drysdale, Small Telescopes & Binoculars, The Proceedings of the Optical Convention, pp. 126-128, Jun. 1905.

Primary Examiner—John K. Corbin
Assistant Examiner—Rodney Bovernick
Attorney, Agent, or Firm—Eugene E. Geoffrey, Jr.

[57] ABSTRACT

An eyeball microscope used for observing cornea endothelcells and the like, having an objective lens structure including an optical tip member which is formed of a material with lower refractive index than glass in order to avoid the undesired effect of reflection of illuminating light from the front surface of the optical tip member, and an adaptor for stably holding an impregnating liquid between the optical tip member and the cornea; the use of which will result in substantial reduction of reflection from the cornea surface and a corresponding increase in the field of view and resolution.

9 Claims, 11 Drawing Figures

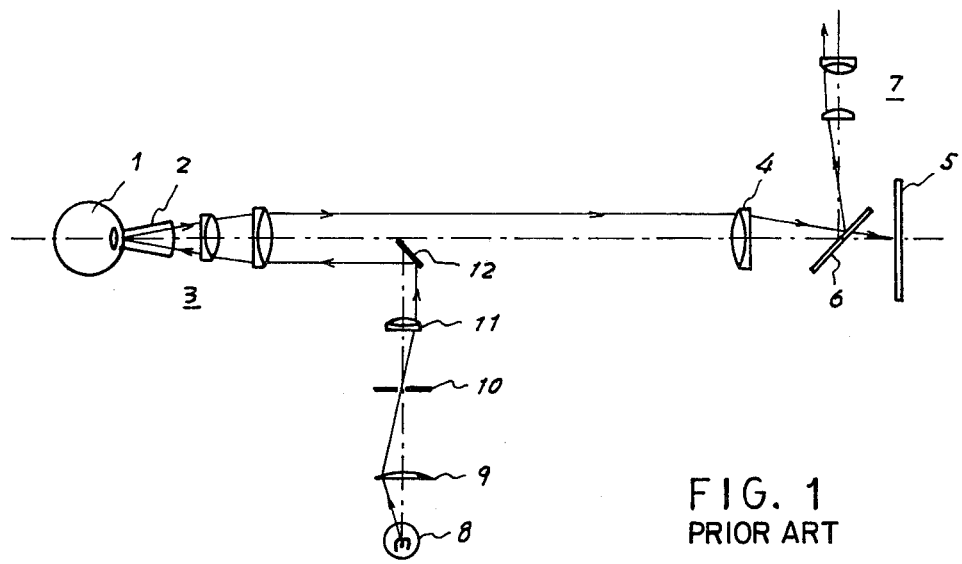
FIG. 1
PRIOR ART
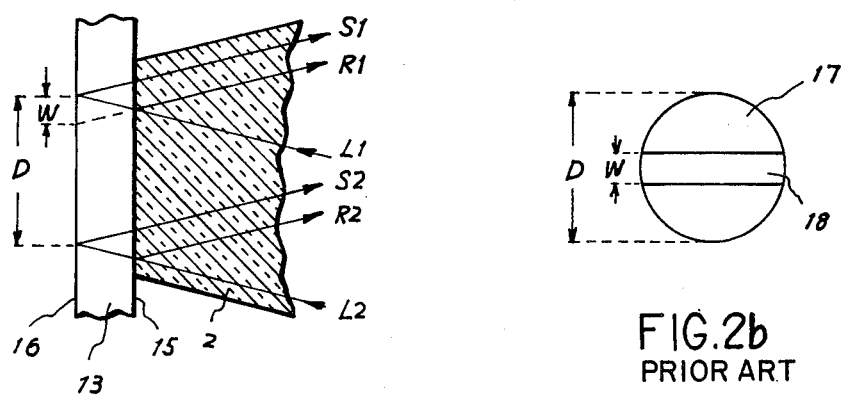
FIG. 2a
PRIOR ART
FIG. 2b
PRIOR ART
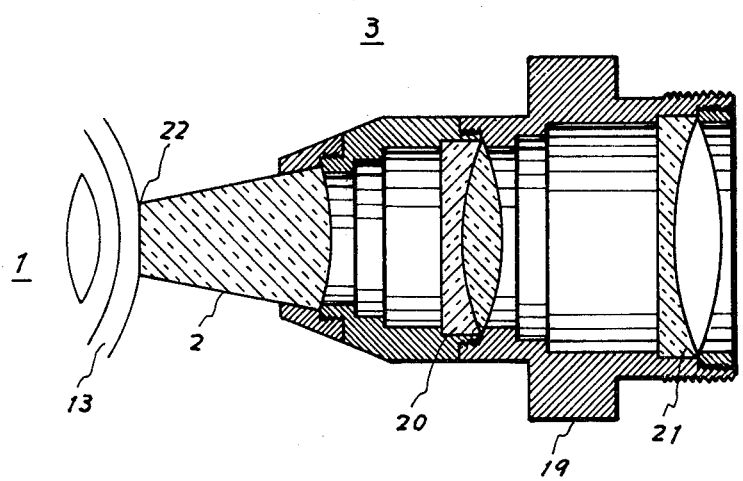
FIG. 3

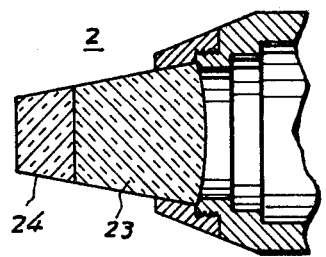
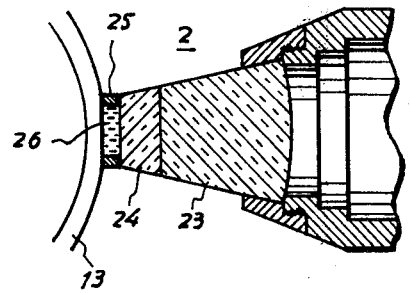
FIG. 4     FIG. 5
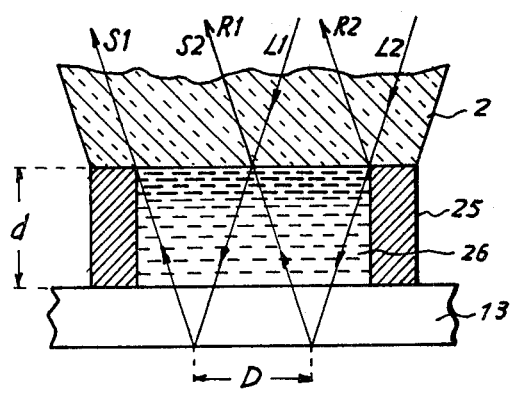
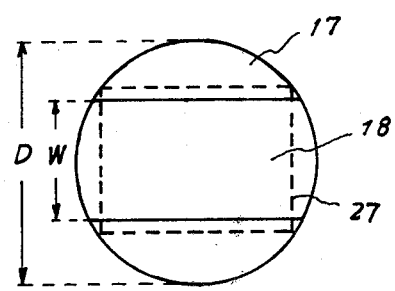
FIG. 6     FIG. 7
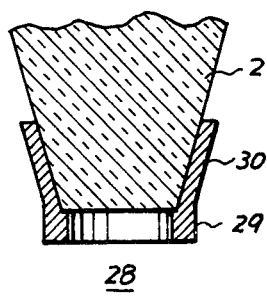
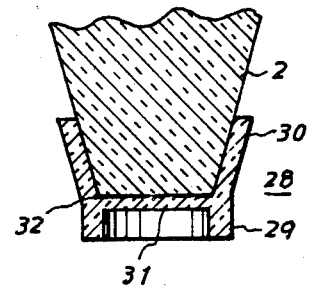
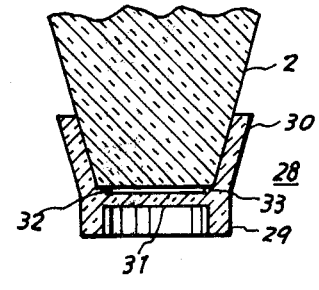
FIG. 8     FIG.9A     FIG.9B

EYEBALL MICROSCOPE

This invention relates to improvement in an eyeball microscope used for observing in magnification the interior of an eyeball.

An eyeball microscope used for observing the interior texture of an eyeball, such as cornea endothelcells, is known in the art and an example thereof is disclosed in Japanese opened patent specification No. 54-99647. As described in this specification, the microscope of this type is provided with an objective lens structure including a glass optical member generally called "cone lens." In observation, the front face of the cone lens is placed in contact with the cornea and illuminating light is introduced from a side of the optical axis of the microscope and projected onto the observed object through the objective lens. However, due to a substantial difference in the refractive index between the glass and the cornea substance, reflection of the illuminating light at the contact surface between the optical tip member and the cornea was not negligible and the reflecting light overlapped with the light from the object which resulted in a reduction in the field of view and resolution.

Accordingly, an object of this invention is to provide an eyeball microscope having an optical tip member which can reduce such undesirable reflection.

In accordance with this invention, the eyeball microscope includes an optical tip member, which is formed of an optical material having lower refractive index than glass, in its objective structure, to reduce the useless interface reflection.

The above and other features of this invention will be described hereinunder with reference to the accompanying drawings.

IN THE DRAWINGS

FIG. 1 is a schematic diagram representing an optical system of a typical eyeball microscope to which this invention is applicable;

FIGS. 2(a) and 2(b) are diagrams illustrative of the relationship between the path of illuminating light and the field of view in a prior art eyeball microscope;

FIG. 3 is a cross sectional view representing an objective lens structure embodying this invention;

FIG. 4 is a cross sectional view representing a variation of the optical tip member in the embodiment of FIG. 3;

FIG. 5 is a cross sectional view representing an improved embodiment in which a front ring for holding impregnating liquid is attached to the embodiment of FIG. 4;

FIGS. 6 and 7 are diagrams illustrative of the relationship between the path of illuminating light and the field of view in the embodiment of FIG. 5;

FIG. 8 is a cross sectional view representing an adaptor according to this invention having the same effect as the embodiment of FIG. 5; and FIGS. 9(a) and 9(b) are cross sectional views representing two improved variations of the adaptor of FIG. 8.

Throughout the drawings, like reference numerals are used to denote like structural components.

Reference is now made to FIG. 1, which shows an optical system of a typical eyeball microscope used for observing the interior of an eyeball 1. The microscope includes an objective lens structure 3 having a cone lens 2, a focusing lens 4 and a photographic film 5 arranged along its main optical axis; and also includes a half-mirror 6 and an eye-piece structure 7 arranged along its monitoring optical axis. The microscope is provided with an illuminating optical system comprising a light source 8, a condenser lens 9, a slit 10, a collimating lens 11 and a mirror 12 arranged laterally to the main optical axis. As shown by arrows in the drawing, the light emitted from the light source 8 is converged through the condenser lens 9 and slit 10, made parallel by the collimating lens 11, reflected by the mirror 12 into the main optical system and projected onto the object in the eyeball 1 through the objective lens structure 3. An optical image produced by this light is transferred in the opposite direction through the objective lens structure 3 and focusing lens 4 and imaged on the photographic film 5, and, at the same time, it is suitably observed through the half-mirror 6 and eye-piece structure 7.

In this instance, according to the prior art, the front surface of the cone lens 2 located at the front end of the objective lens structure 3 has been placed in contact directly or through a very thin layer of impregnating liquid with the cornea. As shown in FIG. 2(a) which is a longitudinal sectional view representing the state of contact, the cone lens 2 of the objective lens structure 3 is in contact with the surface 15 of the cornea 13 and the focus of the microscope is adjusted at the plane of cornea endothelcells 16. With a parallel illuminating light flux L1-L2 from the illuminating system projected onto an area of the object of width D, an optical image flux S1-S2 is obtained from this area and it is reasonable to assume that it should enable observation of the whole field of view 17 with diameter D, as shown in FIG. 2(b). However, reflected light flux R1-R2 is produced at the contact surface 15 between the cone lens 2 and the cornea 13 due to a significant difference in refractive index between the glass constituting the cone lens 2 and the cornea 13. Since the brightness of the reflected light is as high as about ten times the brightness of the optical image of the object, observation is remarkably interfered with except for the area 18 of width W which is not influenced by the reflected light and, moreover, the width is as small as about 20 percent to 25 percent of diameter D. No substantial difference in this condition can be expected even if a thin layer of impregnating liquid is placed between the cone lens and the cornea.

An objective lens structure according to an embodiment of this invention, as shown in FIG. 3, includes a body tube 19, a cone lens 2 and lenses 20 and 21. As a feature of this invention, the cone lens 2 is made of a transparent optical material, such as fluorite CaF or synthetic resin, having lower refractive indices than glass, and is coated with an antireflection coating 22 at the front surface as occasion demands. In case of fluorite, having a refractive index of about 1.43, as the material of the cone lens 2, the interface reflectivity with respect to the cornea which has a refractive index of about 1.37 is as low as about one tenth of that in case of optical glass the refractive index of which is about 1.5 and this results in a remarkable reduction of reflection of the illuminating light. This reduction in reflected light results in an increase in contrast and resultant expansion of field of view.

However, the above low refraction index materials, especially fluorite, are so brittle that they are often broken at the joint to the body tube 19. In addition, they are difficult to handle and relatively expensive as compared with glass. FIG. 4 shows an improved embodiment for overcoming these disadvantages, in which the cone lens 2 consists of a body portion 23 made of optical glass and a tip portion 24 made of the above mentioned low refractive index material is bonded to the portion 23 with a suitable known adhesive. If the thickness of the tip portion 24 is selected suitably large, possible reflection at the interface of the tip and body portions will not affect the observation.

While the antireflection effect is improved by placing an impregnating liquid having refractive index in between the surfaces of the cone lens 2 and the cornea 13, this effect is little. FIG. 5 shows the embodiment of FIG. 4 improved for increasing the thickness of the impregnating liquid layer, in which a short metallic or plastic tubular member 25 is adhered to the front surface of the tip portion 24 of the cone lens 2. When used, impregnating liquid which has refractive index intermediate those of the tip portion 24 and the cornea 13 is filled in the tubular member 25. In case of a tip portion made of fluorite, the impregnating liquid may be physiological saltwater.

While the length of the tubular member 25 or the height of the side wall corresponds substantially to the thickness of the impregnating liquid layer, the layer is less effective if it is too thin as aforementioned. Now, the amount of this thickness which is practically required will be described with reference to FIGS. 6 and 7. FIG. 6 shows a threshold state wherein the inner boundary S2 of an optical image flux S1-S2 produced by an illuminating light flux L1-L2 coincides with the outer boundary R1 of the reflected light flux R1-R2 from the front surface of a cone lens 2. Putting d as the thickness of liquid layer 26, that is, the length of tubular memer 25, it is clear that the optical image will not be affected by the reflected light throughout the field of view with width D if the thickness of liquid layer is greater than d. However, this d is a function of magnification and NA value or numerical aperture of the objective and distance between the cornea surface and the object. In this kind of microscope, NA value of objective is typically 0.2 to 0.4.

In the case of using a most popular objective structure of magnification ×20 and NA value 0.33 and putting the front face of the cone lens in contact with the cornea to observe the endothelcells which is about 0.5 millimeter deep from the cornea surface, the ratio of the width W of field of view of visible image to the width D of whole field of view was 0.2 to 0.25 as aforementioned. However, this ratio was increased to about 0.5, as shown in FIG. 7, by using a liquid layer of 1.0 millimeter thick, even though the same object was observed with the same objective structure. Although the width W of this order would be almost sufficient for photographing in view of the photographic field of view as indicated by dashed line, the whole field of view 17 was covered almost completely by the visible field of view 18 when the thickness of liquid layer was 1.5 millimeters. For practical use, the liquid layer of about 4 millimeter thick will facilitate the handling and observing operations.

While, in the embodiment of FIG. 5, the tubular member 25 for holding impregnating liquid is adhered to the front surface of the cone lens 2, it is difficult to remove bubbles produced in the liquid layer and also inconvenient for cleaning up contamination as the liquid layer becomes thick as above. FIG. 8 shows an adaptor 28 conceived for overcoming these disadvantages. The adaptor 28 is made of metal or plastic and, as shown in the drawing, includes an annular wall portion 29 at the top and a conical portion 30 having an inner surface which fits with the outer surface of the tip portion of the cone lens 2, so that it can be detachably coupled to the cone lens 2. The height of the wall portion 29 is selected in accordance with the aforementioned principle of liquid layer thickness. This adaptor will significantly facilitate the cleaning operation of the inner and outer surfaces of itself and the front surface of the cone lens 2.

FIGS. 9(a) and 9(b) show improvements of the adaptor of FIG. 8. In FIG. 9(a), the adaptor 28 is provided with a circular partition 31 between the wall portion 29 and the conical portion 30 and the whole structure is made of a transparent material having a refractive index which is intermediate those of the cone lens and the cornea. Plastics may be used preferably for this purpose. When the adaptor 28 is used, the gap 32 between the cone lens 2 and the partition 31 is filled which impregnating liquid having refractive index intermediate those of the cone lens 2 and the partition 31 and the interior of the wall portion 29 is preferably filled with impregnating liquid having refractive index nearly equal to that of the cornea. Thus, reflections at the interfaces other than the front surface of the cone lens are almost nullified and interaction of the reflected lights with the optical image is completely prevented.

FIG. 9(b) shows an improvement in the adaptor of FIG. 9(a), wherein a small step 33 is provided along the intersection of the inner surface of the conical portion 30 and the upper surface of the partition 31. This step provides a substantially thick gap 32 constantly maintained between the front surface of the cone lens 2 and the partition 31, thereby preventing undesired optical interaction even if the use of impregnating liquid in the gap 32, as in the embodiment of FIG. 9(a), is omitted.

Since the adaptor 28 as above described is simple in structure and can be mass produced at low cost, it is sometimes more advantageous to scrap it evey time rather than re-using repeatedly after cleaning.

Although the description has been made about the case where a cone lens is used as the optical tip member of the objective lens structure of the microscope, it is well known that the optical tip member may be of different shape, such as plain glass disc, which can hardly be called "cone lens," and it is a matter of course that this invention can cover these microscopes using the other shapes of optical tip member. Moreover, the materials and geometries of all structural components inclusive of the optical tip member of this invention can be optionally and readily selected by those skilled in the art within the scope of this invention as defined in the appended claims.

What is claimed is:

1. An eyeball microscope, comprising an objective structure having an optical tip member, the front surface of which faces an eyeball cornea, wherein said optical tip member is made of a transparent material having refractive index which is intermediate those of the objective structure and cornea.

2. An eyeball microscope, according to claim 1, wherein said optical tip member comprises a tip portion located on the eyeball side and a body portion located in the opposite side, said body portion is made of glass and said tip portion is made of a transparent material having refractive index which is intermediate those of said glass and cornea.

3. An eyeball microscope, according to claim 1 or 2, wherein said optical tip member is provided at the front surface with a short tubular member for holding impregnating liquid.

4. An eyeball microscope, according to claim 3, wherein the wall height of said tubular member is 1.5 millimeters or more.

5. An eyeball microscope, according to claim 1 or 2, wherein said microscope further comprises an adaptor for holding impregnating liquid, said adaptor including a short tubular wall portion extending from the front surface of said optical tip member towards the eyeball and a portion formed continuously with said wall portion so as to detachably fit the outer surface of said optical tip member.

6. An eyeball microscope, according to claim 5, wherein the height of said wall portion is 1.5 millimeters or more.

7. In an optical microscope comprising an objective structure having an optical tip member, the front surface of which faces an eyeball cornea, an adaptor for holding impregnating liquid between said front surface and said cornea, comprising a short tubular wall portion extending from said front surface toward the eyeball, an extending portion formed continuously with said wall portion so as to detachably fit the outer surface of said optical tip member, and a circular partition facing said front surface and disposed between said extending portion and said wall portion, and the whole structure including said partition being formed integrally of a transparent material having a refractive index which is intermediate those of said optical tip member and said cornea.

8. An adaptor, according to claim 7, wherein a step portion for supporting the front surface of said optical tip member is provided along the intersection of the inner surface of said extending portion and the surface of said partition.

9. An adaptor, according to claim 7, wherein the height of said wall portion is 1.5 millimeters or more.

* * * * *